United States Patent [19]
Schael

[11] Patent Number: 4,770,769
[45] Date of Patent: * Sep. 13, 1988

[54] HEMODIALYSIS APPARATUS WITH DEGASSING MEANS FOR THE DIALYSIS SOLUTION

[75] Inventor: Wilfried Schael, Bad Homburg v.d.H., Fed. Rep. of Germany

[73] Assignee: Fresenius Aktiengesellschaft, Bad Homburg, Fed. Rep. of Germany

[ * ] Notice: The portion of the term of this patent subsequent to May 12, 1998 has been disclaimed.

[21] Appl. No.: 755,772

[22] Filed: Jul. 16, 1985

Related U.S. Application Data

[63] Continuation of Ser. No. 613,005, May 21, 1984, Pat. No. 4,530,759, which is a continuation of Ser. No. 406,711, Aug. 9, 1982, abandoned, which is a continuation of Ser. No. 198,912, Oct. 20, 1980, abandoned, which is a continuation-in-part of Ser. No. 069,387, Aug. 24, 1979, Pat. No. 4,267,040.

[30] Foreign Application Priority Data

Sep. 2, 1978 [DE] Fed. Rep. of Germany ....... 2838414

[51] Int. Cl.$^4$ ............................................. B01D 31/00
[52] U.S. Cl. .................................... 210/96.2; 210/104; 210/149; 210/175; 210/188; 210/257.2; 210/258; 210/321.65; 210/416.1; 210/929
[58] Field of Search ................ 210/96.2, 97, 104, 109, 210/137, 149, 181, 188, 195.2, 257.2, 258, 321, 416, 433.2, 927, 929, 175

[56] References Cited

U.S. PATENT DOCUMENTS 3,352,779 11/1967 Austin et al. ................ 210/321.3 X
3,579,441 5/1971 Brown ............................ 210/321 X
3,709,222 1/1973 DeVries ............................ 128/213

(List continued on next page.)

FOREIGN PATENT DOCUMENTS 2544258 4/1977 Fed. Rep. of Germany .
2344297 10/1977 France .
2345165 10/1977 France .
7701451 5/1977 Netherlands .

OTHER PUBLICATIONS

McDonald, H., "An Automatic Peritoneal . . . ", Trans. Am. Soc. Artif. Int. Organs, 1969, vol. 15, pp. 108-111.
Kunitomo, T. et al., "Controlled Ultrafiltration . . . ", Trans. Am. Soc. Artif. Intern. Organs, vol. 23, 1977.
"The Accurate Control of Ultrafiltration", pp. 144-146, *Artificial Organs*, May 1978, vol. 2, by J. Guus Flendrig, Wim M. Carpay, and Wil T. Dekkers.
"Clinical Evaluation of a Pre-set Ultrafiltration Rate Controller Available for Single Pass and Hemodiafiltration Systems", pp. 141-143, Ultrafiltration Rate Controller, May, 1978; by, Kazuo Ota et al., from *Artificial Organs*.
Ivanovich et al., "A Compact Hydraulic Proportioning System for Hemodialysis", Trans. Am. Soc. Int. Organs., vol. 12, pp. 357 to 361, (1966).

*Primary Examiner*—Barry S. Richman
*Assistant Examiner*—Richard D. Jordan
*Attorney, Agent, or Firm*—W. G. Fasse; D. H. Kane, Jr.

[57] ABSTRACT

The ultra-filtration in a hemodialysis operation is controlled by a control apparatus which is connected to a balancing device (1) and to a dosing device (9) to form a closed loop control circuit for the metered supply of dialysis concentrate into the balancing device and for the metered supply of fresh dialysis solution into the dialyzer. The closed loop control circuit controls the alternating supply of fresh dialysis solution into one chamber of a balancing device and the withdrawal of used-up dialysis solution from the other chamber of the balancing device. The closed loop control circuit also controls a pump for the metered withdrawal of used-up dialysis solution out of the dialysis circulatory system. The dosing device operates as a proportionality device to produce fresh dialysis solution from water and dialysis concentrate whereby the concentrate is dosed and the dialysis solution is also dosed or metered.

13 Claims, 8 Drawing Sheets

U.S. PATENT DOCUMENTS

| | | | |
|---|---|---|---|
| 3,795,318 | 3/1974 | Crane et al. | 210/321.3 |
| 3,844,940 | 10/1974 | Kopf et al. | 210/22 |
| 3,920,556 | 11/1975 | Bowman | 210/321 |
| 3,939,069 | 2/1976 | Granger et al. | 210/90 X |
| 3,946,731 | 3/1976 | Lichtenstein | 210/87 X |
| 3,976,574 | 8/1976 | White | 210/188 |
| 3,979,284 | 9/1976 | Granger et al. | 210/321 X |
| 3,990,973 | 11/1976 | Boag et al. | 210/87 |
| 4,008,003 | 2/1977 | Pinkerton | 417/250 |
| 4,021,341 | 5/1977 | Cosentino et al. | 210/321.3 X |
| 4,037,616 | 7/1977 | Pinkerton | 210/929 X |
| 4,054,522 | 10/1977 | Pinkerton | 210/188 |
| 4,060,485 | 11/1977 | Eaton | 210/87 |
| 4,083,777 | 4/1978 | Hutchisson | 210/85 X |
| 4,093,545 | 6/1978 | Cullis | 210/136 X |
| 4,096,059 | 6/1978 | Pinkerton | 210/647 |
| 4,113,614 | 9/1978 | Rollo et al. | 210/647 X |
| 4,119,113 | 10/1978 | Meginniss, III | 210/321 X |
| 4,137,168 | 1/1979 | Perrot | 210/96.2 |
| 4,153,554 | 5/1979 | Von Der Heide et al. | 210/92.2 X |
| 4,162,974 | 7/1979 | Pernic | 210/321.3 X |
| 4,178,240 | 12/1979 | Pinkerton | 210/637 X |
| 4,209,391 | 6/1980 | Lipps et al. | 210/188 X |
| 4,221,543 | 9/1980 | Cosentino et al. | 417/22 |
| 4,267,040 | 5/1981 | Schal | 210/149 X |
| 4,530,759 | 7/1985 | Schal | 210/257.2 X |

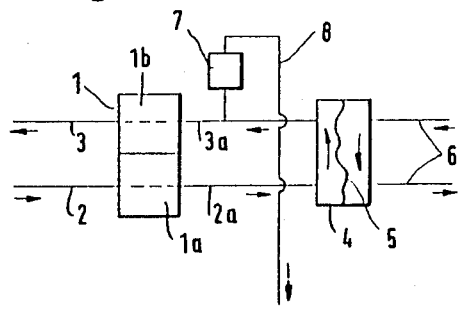
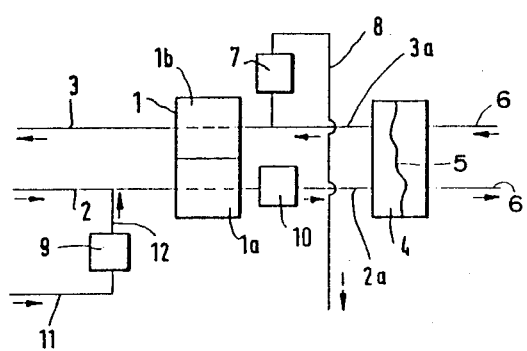

HEMODIALYSIS APPARATUS WITH DEGASSING MEANS FOR THE DIALYSIS SOLUTION

CROSS-REFERENCE TO RELATED APPLICATIONS

The present appplication is a continuation of Ser. No. 613,005, filed May 21, 1984, now U.S. Pat. No. 4,530,759, issued July 23, 1985. Ser. No. 613,005 is a continuation of then copending Ser. No. 406,711, filed Aug. 9, 1982, now abandoned. Ser. No. 406,711 was a continuation of then copending Ser. No. 198,912, filed on Oct. 20, 1980, now abandoned. Ser. No. 198,912 was a continuation-in-part of then copending Ser. No. 069,387, filed Aug. 24, 1979, now U S. Pat. No. 4,267,040, issued on May 12, 1981. The above applications correspond to German patent Application No. P 28 38 414.7, filed in the Federal Republic of Germany on Sept. 2, 1978. The priority of the German filing date is claimed for the present application through the uninterpreted chain of cases listed above.

BACKGROUND OF THE INVENTION INCLUDING PRIOR ART STATEMENT

The invention relates to a control of the ultra-filtration in connection with hemodialysis. A control apparatus controls the alternate supply or withdrawal of fresh and used dialysis solution into one or the other or out of one or the other chamber of at least one balancing apparatus and for controlling the drive of an ultra-filtration pump for an additional withdrawal of used dialysis solution out of the dialyzer circulatory system.

A known method for the discontinuous measuring of the liquid withdrawal per unit of time resides in that the dialyzer solution flow to the dialyzer is temporarily interrupted by means of switch-over valves and in that the outflow conduit of the dialyzer is connected with a through flow meter for reading the liquid withdrawal per unit of time. By means of additional steps the pressure difference beween the blood side and the dialyzing solution side is kept constant on the previous operational value. Thus, the passage of liquid through the membrane during the measuring is about the same as during the normal operation. It is disadvantageous, that each time it is necessary to interrupt the operation so that a continuous measuring is not possible according to said method. Further, with said method only one measuring possibility is provided. In order to achieve a determined value of the liquid quantity to be withdrawn it is necessary to evaluate the measured results and to make a corresponding manual correction of the operating values in the apparatus at relatively short time intervals.

It is known from U.S. Pat. No. 4,113,614 to automate the control of the pressure across the membrane in a hemodialysis apparatus and also to automate the control of the ultra-filtratior rate by metering and monitoring the ultra-filtration rate and the total quantity of ultra-filtrate removed. One embodiment of this U.S. Pat. No. 4,113,614 which was issued on Sept. 12, 1978, requires a dialysis solution reservoir having a constant volume. In another embodiment of this prior art two pumps are used having exactly corresponding pumping rates for the supply and discharge of dialysis solution, whereby a dynamically closed system is provided. However, it is in practice very difficult to construct pumps in an economically feasible way, which have exactly corresponding pumping rates.

U.S. Pat. No. 4,113,614 also discloses a special pump for the withdrawal of liquid from the dynamically closed system in such a quantity that the quantity of withdrawn liquid corresponds to the ultra-filtration quantity. A piston pump is disclosed for this purpose which is also utilized simultaneously for r:easuring the pumped quantity and, based on the assumed proportionality of the driving force for the pump and the working pressure of the pump, for measuring the pressure. This type of apparatus leaves room for improvement, especially with regard to the problem of proportioning the concentrate and water. More specifically, the preparation of the dialysis solution from concentrate and water in exactly predetermined ratios in combination with the supply and removal of liquid quantities corresponding to each other may be improved upon, particularly if these mentioned partial functions are to be directly combined or linked with each other as is the purpose of the present invention.

An article by Harold P. McDonald, Jr., entitled "Automatic Peritoneal Dialysis Machine for Hospital or Home Peritoneal Dialysis; Preliminary Report" appeared in volume 15 of the "Transactions of the American Society of Artificial Internal Organs", (1969) starting at page 108 and ending on page 111. A peritoneal dialysis apparatus is not necessarily suitable for hemodialysis purposes. For example, in a peritoneal dialysis apparatus a single state system is used in a discontinuous operation with piston pumps. The ultra-filtration is not controlled and the ultra-filtrate quantity may be measured only at certain times, namely, at the end of the flow out time by measuring the liquid level in the flow out container. Thus, the teachings applicable to a peritoneal dialysis apparatus are not suitable for a hemodialysis apparatus especially where the latter is supposed to operate continuously in a push-pull fashion to assure a continuous, uniform flow through the dialyzer. Moreover, the control of the ultra-filtration with a predetermined ultra-filtration rate in terms of ultra-filtration quantity per unit of time, as well as a continuous indication of the accumulated ultra-filtration quantity, is not taught by McDonald, Jr.

U.S. Pat. No. 4,037,616 (Pinkerton) discloses certain features which are also employed according to the present invention, for example, the use of balancing chamber components operated in a push-pull type of system. However, Pinkerton actually uses the diaphragms and piston means or at least piston rods which extend through the chamber walls and thus cause leakage problems at the points where the piston rods extend through the chamber walls, see for example FIGS. 1, 3, and 4 of Pinkerton. The type of liquid used in dialysis comprises a high proportion of salt and glucose in solution. Therefore, there is a strong tendency for these components in solution to crystallize, and experience has shown that such crystallization takes place on the piston rods, whereby the sealings at the passage points through the chamber walls are damaged by the crystalline material. This crystallization is a continuous process and once a leakage has formed it grows rapidly.

Moreover, in this environment it is, for the patient's health, very important to keep the entire system free of infection causing agents. Piston rods as in Pinkerton cannot be kept entirely free of such infecting agents because the piston rods extend into and out of the balancing chamber components.

Kunitomo et al in the article "Controlled Ultrafiltration With Hemodialysis", Trans. Am. Soc. Int. Organs, Volume 23, pages 234 to 242 (1977) also do not disclose the combination of teachings for the proportional mixing of the two components which are used to make fresh dialysis solution and there is also no teaching in Kunitomo et al to combine the mixing with a balancing operation. While it is true that Kunitomo et al disclose a degasser in FIG. 2 on page 235, applicant does not claim a degasser per se.

A second Pinkerton U.S. Pat. No. 4,054,522 also suffers the same defects as the first mentioned Pinkerton reference (U.S. Pat. No. 4,037,616) and the comments above apply also to the second Pinkerton reference including FIG. 3 thereof.

U.S. Pat. No. 3,976,574 (White) shows two degassers (22) and (26). However, these two degassers or aerators are connected in series through the mixer (24) and hence both aerators are effective on the liquid which is supplied to the dialyzer (10). According to the present invention the aerators or degassing means are arranged quite differently. The present invention is more importantly concerned with balancing and ultra-filtration control.

U.S. Pat. No. 3,795,318 (Crane et al) was primarily cited for its pressure sensing features. However, the present invention is not exhausted by such a feature and aims at a switch-over of the balancing chamber components from push to pull and vice versa in response to a pressure sensing. Thus, the respective valve means at the inlets of the balancihg chamber components are switched from one into the other position if the pressure in the return conduit from the dialyzer at the outlet of the pump (67) in FIG. 8 exceeds a predetermined pressure value.

The control of a switch in response to a pressure sensitive element is shown in U.S. Pat. No. 3,709,222 (DeVries) "Method And Apparatus For Automatic Peritoneal Dialysis", however, the just mentioned reference does not disclose the combination of the features set forth hereafter. Therefore, even if the disclosure of DeVries is combined with the disclosure of the Pinkerton reference U.S. Pat. No. 4,037,616 the teachings of the present inventicn cannot be found.

U.S. Pat. No. 4,060,485 (Eaton) shows the use of a "computer" in a dialysis apparatus. However, there are no details shown in the Eaton reference to the effect that two temperature controlled heating units are employed for improving, or rather increasing the balancing precision as disclosed with reference to present FIG. 4. The present temperature controlled system of the present application assures that the temperature difference between the inflowing and outflowing dialysate is substantially zero and that the temperature of the dialysate in the dialyzer corresponds to the patient's temperature. No such teaching is disclosed by Eaton.

U.S. Pat. No. 4,113,614 shows an ultra-filtration rate read-out unit. However, the present invention is not exhausted by such a feature.

U.S. Pat. No. 3,352,779 discloses the filling of the hemodialyzer prior to its operation. While it is necessary to fill the dialyzer prior to its operation, Austin et al do not give any hint of the specific way this is accomplished according to the present invention.

U.S. Pat. No. 4,054,522 shows, in FIG. 3, the sequential arrangement of a dosing and mixing system (A) with a degassing system (B) and the ultra-filtration system (C). These three systems (A, B, and C) of U.S. Pat. No. 4,054,522 operate substantially independently of one another. Therefore, the cooperation as set forth in the present case of the proportioning and mixing system with the remaining features is not disclosed in U.S. Pat. No. 4,054,522. According to the present invention the concentrate only is directly dosed and the water is dosed indirectly. The balancing system acts as a meter for the quantity of used-up dialysis solution whereby a connection between the balancing function and the proportioning is accomplished. This is not shown in U.S. Pat. No. 4,054,522.

French patent No. 2,344,297 shows the use of an alarm in a hemodialysis system when the blood transfer level is not acceptable. Although this French patent shows two balancing chambers, it does not disclose the functional or operational combination of the balancing operation with the dosing and mixing operation. Further, the detector in French reference No. 2,344,297 is a hemoglobin detector in the form of a "colorimeter 23" which cannot be compared with the present blood leakage detector (65) in FIG. 8.

German patent Publication No. 2,544,258 which is based on another invention of the present inventor, was also cited for the alarm feature. In this earlier system, of the present inventor, the operation is not a push-pull operation so that a filling step is required between two working steps or strokes. During the filling step dialysate does not flow through the dialyzer. Mcreover, the balancing is not directly related to the dialysis solution as it is prepared and flowing into the dialyzer. In this reference the components of water and concentrate on the one hand, and the used-up dialysis solution on the other hand, are balanced.

In French patent No. 2,345,165 the production of the dialysis solution with the step of proportional mixing of the concentrate and water is independent of the balancing and independent of the ultra-filtration control. Therefore, a more detailed discussion of this reference does not appear to be necessary.

Netherlands' patent Publication 7,701,451 appears to be quite similar to the Pinkerton reference U.S. Pat. No. 4,037,616 which has been discussed in detail above. Therefore, a further discussion of the Dutch reference would appear to be unnecessary.

Ivanovich et al in the article "A Compact Hydraulic Proportioning System For Hemodialysis", Trans. Am. Soc. Int. Organs, Vol. 12, pages 357 to 361 (1966) provides an alternative to the French patent No. 2,344,297 with regard to the alarm feature and is pertinent only to that feature. Therefore, a further discussion of this Ivanovich et al reference does not appear to be necessary. Furthermore, in Ivanovich et al the water and concentrate are dosed by piston pumps. Contrary thereto according to the present invention, the through flow of the ready dialysis solution already mixed is measured and this measuring controls the portion-wise supply of the concentrate to a mixing point arranged upstream of the balancing chamber.

Applicant notes the following additional references, all of which may be clearly distinguished from the present invention:

U.S. Pat. Nos:

3,920,556 (Bowman);
3,939,069 (Granger et al);
3,979,284 (Granger et al);
3,990,973 (Boag et al);
4,008,003 (Pinkerton);

4,021,341 (Cosentino et al);
4,083,777 (Hutchisson);
4,093,545 (Cullis);
4,096,059 (Pinkerton);
4,119,113 (Meginniss, III);
3,946,731 (Lichtenstein);
3,579,441 (Brown); and
3,709,222 (DeVries).

OBJECTS OF THE INVENTION

In view of the above it is the aim of the invention to achieve the following objects singly or in combination:

to construct a hemodialysis apparatus so that the dosing of fresh dialyzing liquid to be supplied takes place automatically on the basis of the operation of a balancing apparatus and to make possible a continuous display or control of the rate of ultra-filtration;

to provide a control circuit for a hemodialysis apparatus which responds either to the throughput of certain volumes or masses of the dialysis solution or it may respond to a pressure difference caused by volume or mass differences;

to effectively remove gas bubbles especially air bubbles from the entire circulatory system thereby to increase the efficiency of the dialyzing operation;

to control the push-pull type of operation of the dialysis solution balancing system by means of valves which may be switched by electric or electronic control signals;

to provide a continuous flow of dialysis solution by means of passively operated, fixed volume membrane pumps whereby piston operations and the respective leakage problems are avoided;

to supply the components for making the dialysis solution under reduced pressure or atmospheric pressure at the most and to supply the fresh dialysis solution at a pressure larger than atmospheric pressure; and to keep the circuits for fresh dialysis solution hermetically sealed from the circuits for the used dialysis solution to avoid any dangerous infection.

SUMMARY OF THE INVENTION

According to the invention there is provided an apparatus for the ultra-filtration control in a hemodialysis operation in a dialysis circulatory system including a dialyzer, wherein control means control the alternate supply or discharge of fresh and used-up dialysis solution into one or into another or out of one or out of the other chamber of at least one balancing device, said control means also controlling the drive of an ultra-filtration pump for the additional withdrawal of used-up dialysis solution out of the dialysis circulatory system, wherein the control means are connected with a balancing device and with a dosing apparatus for the supply of the dialysis concentrate, whereby a control unit including a control circuit is formed.

BRIEF FIGURE DESCRIPTION

In order that the invention may be clearly understood, it will now be described, by way of example, with referenr:e to the accompanying drawings, wherein:

FIG. 1 is a simplified basic diagram of the dialysis solution circulatory system with a balancing device;

FIG. 2 shows a simplified basic diagram of the dialysis solution circulatory system in which the functions of the balancing and of the proportional dosing are combined and in which both functions are monitored in common;

Figure 3:
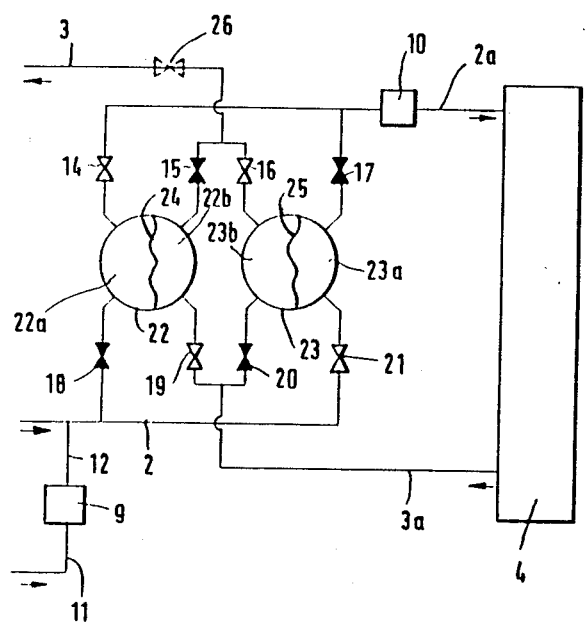
FIG. 3 is a more detailed illustration of the schematic diagram according to FIG. 2.

DETAILED DESCRIPTION OF PREFERRED EXAMPLE EMBODIMENTS AND OF THE BEST MODE OF THE INVENTION

The relevant portion of the liquid circulatory system in FIG. 1 is shown substantially simplified and schematically for explaining the principle of operation of a balancing device. The alancing device 1 is an important component of this arrangement. The balancing device comprises two chambers 1a and 1b connected to each other. The first chamber 1a cooperates with the supply conduit 2 for the fresh dialysis solution. The second chamber 1b cooperate with the discharge conduit 3 for the used-up dialysis solution. The balancing device makes sure that the quantity of the fresh dialysis solution flowing through the conduit 2a to the dialyzer 4 corresponds exactly to the used-up dialysis solution flowing out of the dialyzer through the conduit 3a. Due to this characteristic of the balancing device it is not possible that under these conditions a volume shift between the blood side of the semi-permeable membrane 5 and the dialysis solution side of this membrane takes place in the dialyzer 4. Such shift cannot take place in one or the other direction. The other side of the membrane 5 is connected to the patient through the conduits 6.

Thus, the so-called ultra-filtration rate is zero. The portion of the liquid circulatory system enclosed between the balancing device 1 and the dialyzer 4 acts as a closed system having a constant volume. A withdrawal device 7 is connected to a discharge conduit 8 in order to remove liquid from this system.

The liquid quantity removed from the system by means of the withdrawal device must be replaced by an equal liquid quantity due to the mentioned characteristics of the balancing device, said liquid quantity passing from the blood side to the dialyzing solution side of the dialyzer membrane. Thus, the liquid quantity removed by means of the withdrawal device corresponds to the liquid quantity passing through the membrane of the dialyzer 4 and thus it corresponds to the ultra-filtrate. The withdrawal device may now be constructed so that a control of the ultra-filtration may be achieved. According to the invention, the ultra-filtrate withdrawal device is, for example, a constant volume membrane pump. The rate of pumping and therefore the rate of ultra-filtration may be automatically controlled in response to measured parameters of the dialysis circulatory system for optimum levels by computer means or analog feedback signal means.

The precision of the balancing device must meet very high requirements. Typically, about 200 liters of the dialysis solution are passed through the dialyzer during a hemodialysis treatment. The ultra-filtration quantity corresponds typically to about 2 to 3 liters. This quantity should be determinable except for a deviation in the order of 0.1 to 0.2 liters. Thus, the balancing error caused in the balancing device should not, if at all possible, exceed the order of 1 per mill (one per thousand). The patient may be exposed to a substantial danger if a larger balancing error occurs and remains unnoticed due to a technical error, for example, due to the failure of a structural component. Thus, it is necessary that the balancing device satisfies the requirement that a functional error is automatically detected and that an alarm is given if an error occurs.

In the present type system the necessary safety against functional failure of the balancing system is achieved in that the balancing unit is not only constructed for the balancing of the inflow and outflow of the dialysis solution, but also it is simultaneously connected to the dosing device to form a control circuit or unit.

The principle of a correspondingly extended arrangement is illustrated in FIG. 2. The same components are provided with the same reference symbols as in FIG. 1.

Additional elements for realizing a proportional dosing function and for monitoring the proportional dosing function comprise a dosing apparatus 9 and an analyzing device 10. The dosing apparatus 9 is supplied through a conduit 11 and in turn supplies into the conduit 2 through a connection 12. The analyzing device is connected directly into the conduit 2 between the balancing chamber 1 and the dialyzer 4.

It is a requirement for the intended function of the illustrated arrangement that the balancing device 1 has a periodic type of operation in which the balancing device passes on a precisely defined dialysis solution volume for each operating period. For this defined dialysis solution volume a volume of concentrate is necessary which has a fixed ratio to the defined dialysis solution volume. The volume of concentrate is supplied also through the dosing device 9 in a periodic manner whereby the balancing device 1 and the dosing apparatus preferably operate in synchronism with each other.

The water supplied through the conduit 2 and the concentrate supplied by the dosing apparatus 9 form, after their mixing, a dialyzing solution of the desired composition if the quantitative ratio has been correctly adjusted. The composition is monitored by the analyzing device connected into the conduit to the dialyzer.

The components serving in the balancing device for the metering of the volumes simultaneously determine the liquid volume conveyed during each working period. Therefore, it is possible, by using the analyzing device 10 to monitor the operation of the proportional dosing as well as indirectly the operation of the balancing.

Details shall be explained with reference to the example illustrated in FIG. 3. The balancing device comprises the balancing chambers 22 and 23 and the respective valves 14 to 21. The balancing device forms together with the dosing apparatus 9 a proportional dosing system which mixes the concentrate and water in a predetermined quantity ratio. The analyzing device 10 measures one or several parameters which are characteristic for the composition of the mixture, whereby a control of the mentioned functions is possible. For example, an output of the analyzing device 10 is connected for controlling a valve 62 as shown by the dashed line 83' in FIG. 8.

Both chambers 22 and 23 are an essential component of the balancing device. Basically, these chambers comprise fixed volume hollow bodies each including two spaces which are separated from each other by a movable, tightly closing flexible element 24 or 25. Thus, when one of the spaces is increased in size, the size of the other space is necessarily reduced to the same extent. In the schematic illustration of FIG. 3 the chambers 22 and 23 are, for example, spheres, and the movable elements 24 and 25 are membranes. Having regard to the dosing function, it is further important for the actual construction of the chambers and the elements movable therein that the displacement of the movable elements from one extreme position into the other results in a reproduceable volume displacement.

This feature is achieved, for example, in the embodiment of FIG. 3 in that the membranes 24 and 25 in their extreme positions rest completely against the right or left wall of the respective chamber so that upon movement from one extreme position into the other a volume shift takes place corresponding in its value to the entire chamber volume.

The valves 14 to 21 arranged for cooperation with the balancing chambers, form two groups which are operated alternately. If the valves of the group A (valves 15, 17, 18, and 20) are opened, the valves of the group B (valves 14 16, 19, and 21) are closed and vice versa. Thus, the two chambers operate in push-pull fashion whereby their respective functions are periodically exchanged. During the time when one of the two chambers is respectively connected into the circulatory system 2a, 3a of the dialyzer, the other chamber is charged with new dialysis solution while simultaneously the used-up dialysis solution is displaced into the discharge conduit 3.

If the valves of the group A (illustrated in dark) are opened, and if the valves of the group B (lightly illustrated) are closed, the chamber 22 is charged with fresh dialysis solution while the chamber 23 serves for supplying the dialyzer. The charging of the chamber 22 is achieved due to the fact that fresh solution flows under pressure through the opened valve 18 into the space 22a. Thus, the membrane 24 yields and the used dialysis solution present in the space 22b on the other side of the membrane is displaced through the opened valve 15 into the discharge conduit 3. When the membrane rests entirely against the right-hand chamber wall, this charging operation is completed.

During this time the dialyzer is supplied from the chamber 23 in that the fresh dialysis solution present in the space 23a is conducted through the opened valve 17 and through the conduit 2a to the dialyzer. This solution is returned as used-up dialysis solution from the dialyzer through the conduit 3a and the opened valve 20 into the space 23b of the same chamber. Due to the fixed volume of the balancing chamber the returned quantity of liquid must necessarily correspond exactly to the quantity of liquid supplied into the dialyzer. The dialyzing solution flows thus in a quasi-closed circulatory system because the beginning and the end are connected to each other in the balancing chamber by means of the displaceable element. However, a mixing of fresh and used-up dialysis solution does not take place. As soon as the membrane in the chamber 23 rests completely against the right-hand chamber wall the operation is completed. In order to maintain the through flow through the dialyzer, merely, the valves are switched over so that the two chambers of the balancing device exchange their function.

If now the valves of group A are closed and the valves of group B are opened, fresh dialysis solution may continue to flow to the dialyzer through the opened valve 14 from the space 22a of the chamber 22. During this time the same quantity of used-up dialysis solution is returned out of the dialyzer through the opened valve 19 into the space 22b on the other side of the membrane. At the begining of this operation the space 22a is in its maximally filled condition whereas the space 22b is in its minimally filled condition because during the preceding work period the space 22a was filled completely with fresh dialysis solution as described. During the time when the dialyzer is supplied from the chamber 22, the chamber 23 is being charged with fresh dialysis solution. At the beginning of this time the space 23b is filled completely with used-up dialysis solution as the result of the preceding work period. The fresh dialysis solution flows through the opened valve 21 into the space 23a and the used-up dialysis solution present in the space 23b is displaced through the opened valve 16 into the discharge conduit 3.

The switch over of the valve groups must respectively occur when the supply in the balancing chamber which presently feeds into the dialyzer, is exhausted. The charging of the other balancing chamber should be completed at this time. Such completion may be achieved by a respectively high charging speed without difficulties. The signal for the switch over of the valves may be obtained in different ways. The flow of dialysis solution in the dialyzer circuit stops as soon as the membrane in the balancing chamber which feeds the dialyzer reaches its extreme position. Therefore, it would be possible to use a through flow meter with a device for providing a signal output when the flow falls below a minimum flow. Another approach uses pressure responsive end position sensing using the pressure change resulting as the membrane reaches the end position for triggering the switch over function. Further, known methods may be employed which provide a direct indication when the membrane reaches the end position, for example, micro-sensors may be used.

The balancing device takes up a certain quantity of dialysis solution during each working stroke or period when it is working as described. This quantity of dialysis solution is defined by the volume shift occurring due to the two extreme positions of the movable element in the balancing chamber. For each volume unit taken up by the balancing device, it is necessary to supply the respective quantity of concentrate to the supplied basic liquid (for example, distilled water) in order to produce by mixing the concentrate and the liquid in the intended ratio, the dialysis solution having the desired composition and concentration. The addition of the concentrate is accomplished by the dosing apparatus 9. The dosing apparatus may, for example, be constructed as a dosing pump which supplies by means of one or several pump strokes the quantity of concentrate necessary for one filling of the balancing chamber. The operation of the dosing apparatus is controlled in synchronism with the switching over of the valves 14 to 21. Stated differently, during each charging operation of one of the balancing chambers 22 or 23 the required quantity of concentrate is called up and mixed into the water flowing in simultaneously. In FIG. 3 the mixing conduit is directly connected to the supply conduit 2 of the balancing device. However, this is not at all necessary. It may be more advantageous to carry out the mixing of the concentrate into the water in a component preceding the water treatment system proper or the mixing may be done directly at the water inlet of the apparatus, among others, for the purpose of achieving an intermixing of the concentrate and the water which is as homogeneous as possible.

The analysis device 10 monitors in a manner known as such the composition of the dialysis solution which flows to the dialyzer. It is cusomary to use for this purpose a meter measuring the electrical conductivity. However, other analysis devices may be employed, for example, ion selective electrodes. However, it is essential that in an apparatus according to the invention now only the function of the proportional dosing of concentrate and water is monitored with the aid of the analysis device, but indirectly also the balancing function. That is to say, if a defect should occur in one of the structural components of the balancing device, for example if one of the valves 14 to 21 fails, or if one of the membranes 24, 25 springs a leak, or if the balancing chamber springs a leak outwardly, the dosing function is impaired thereby which results in a corresponding deviation of the composition of the dialysis solution. In such instances an alarm signal is caused by the customary limit value monitoring of the analysis device. In addition, the apparatus may be automatically switched off in order to prevent further effects of the fault.

The arrangement illustrated in FIG. 3 has a further important characteristic in that it provides the possibility to temporarily suspend the balancing function while simultaneously maintaining the functions of the proportional dosing of concentrate and water. For example, this is important when a new dialyzer is put into operation in order to initially fill the dialyzer with dialysis solution. Due to the characteristic features of the balancing system such initial filling would normally not be possible because the balancing system discharges a quantity of liquid equal to the liquid supplied into the balancing system thereby keeping the liquid volume in the dialyzer circulatory system constant.

The operation in which the balancing function is suspended is accomplished by a different control of the valves. Starting with a condition in which one of the balancing chambers (for example 22a) is completely filled with fresh dialysis solution and the other balancing chamber (for example, 23b) is completely filled with used dialysis solution, the valves 19 and 20 and a valve 26 in the discharge conduit are closed. The valves 15 and 16 are opened and the valves 16 and 17 as well as 21 and 14 form two groups which are opened and closed in alternating sequence. The control of the mentioned valve groups may be accomplished on the one hand in the above described manner in response to the detection of the extreme positions of the membrane, more simply, by means of a time clock pulse which is selected to be sufficiently slow so that the membranes will be in their end positions with certainty at the time of the switch over.

When the valves 21 and 14 are being opened under the mentioned conditions while the valves 18 and 17 are closed, fresh dialysis solution flows through the valve 21 into the space 23a of the balancing chamber 23 thereby displacing out of the space 23b on the other side of the membrane a respective quantity of the liquid through the opened valves 15 and 16 into the space 22b of the balancing chamber 22. As a result, an equal quantity of fresh dialysis solution is displaced out of the space 22a and supplied through the opened valve 14 to the dialyzer. This operation ends when the membranes reach their extreme positions.

Thereafter the valves 21 and 14 are closed and the valves 18 and 17 are opened. The fresh dialysis solution now flows through the valve 18 into the space 22a of the balancing chamber 22 and displaces through the membrane the solution present in the space 22b through the opened valves 15 and 16 in the space 23b of the balancing chamber 23 whereby the fresh dialysis solution previously filled into the space 23a is transmitted in equal quantity through the valve 17 to the dialyzer. After the membranes have reached their extreme positions, a new switch-over of the valve groups 18 and 17, and 21, 14 takes place so that the two chambers 22, 23 again exchange their functions.

By the described manner of operation the dialysis solution is transmitted to the dialyzer in determined portions as in the normal, balancing type of operation. These portions are defined by the volume shift which occurs between the two extreme positions of the movable element in the balancing chambers. The dosing apparatus supplies the concentrate in synchronism. Thus, the function of the proportional dosing of water and concentrate remains in existence while the balancing is suspended.

Figure 3A:
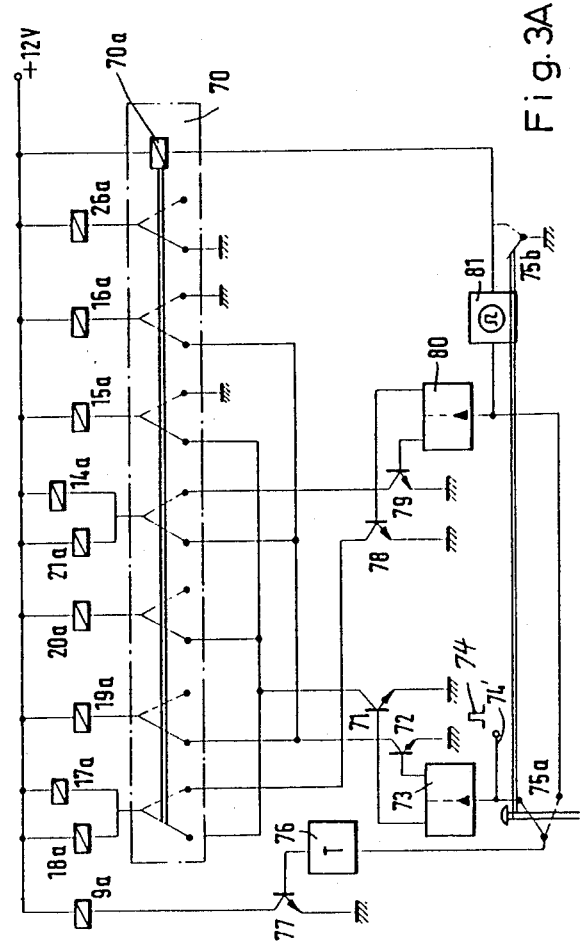
FIG. 3A is a circuit arrangement for controlling the balancing device and the dosing apparatus.

A circuit arrangement for controlling the valves 14 to 21 and 26 as well as the dosing apparatus 9 in accordance with the described function is shown in FIG. 3A. In this connection it is to be noted that merely a simple example embodiment is involved which may be replaced by other circuit arrangements in a different manner. If the operation of the valves and of the dosing apparatus does not take place by means of solenoids as is assumed herein, but rather, for example, by hydraulic or pneumatic means, it is possible to use control devices which operate in an equivalent manner according to the general state of the art without any difficulties.

The switch over from the normal balancing type of operation to the non-balancing type of operation takes place by means of a relay 70 having seven switch-over contacts to the terminals of which the solenoids of the valves 14 to 21 are connected. In the illustrated rest position of the contacts the solenoids 14a to 21a and 26a of the valves 14 to 21 and 26 are coordinated in two groups which are alternately supplied with current through the respective power amplifier 71 or 72 by means of a flip-flop 73.

The control signals from the end position detector of the balancing device are supplied through the conductor 74. They reach the power amplifier 77 for activating the solenoid 9a of the dosing apparatus 9 through a selector switch 75a and a timer 76 which produces a pulse or a pulse sequence of a determined duration. Thus, a dosing operation is caused for each switch over.

In order to switch the system over into the non-balancing type of operation, the mechanically coupled selector switches 75a and 75b are brought into the position illustrated by a dashed line. Thus, the solenoid 70a of the relay 70 conducts current so that the selector contacts thereof also take up the positions illustrated by dashed lines. The solenoids of the valves 19, 20, and 26 thus become de-energized so that these valves remain continuously closed. The solenoids of the valves 15 and 16 receive continuously the energizing current in order to keep these valves open.

The valve groups 18, 17 and 21, 14 are alternately switched over by the flip-flop 80 through the power amplifier 78, 79. The control of the flip-flop 80 is accomplished by an impulse generator 81 which has been energized by actuating the selector switch 75b into the active state. The control pulses are simultaneously supplied to the solenoids 9a of the dosing apparatus 9 through the selector switch 75a, the timer 76 and the power amplifier 77 so that the dosing apparatus 9 continues to operate synchroneously with the switch over steps of the balancing device.

A further embodiment of the invention provides the possibility to reference the balancing to the mass of the inflowing and outflowing liquid. This is accomplished in that the temperatures of the liquid flows in the balancing device are made to correspond to each other whereby the influence of the dependency of the density of the liquid is eliminated. An arrangement for accomplishing this purpose is illustrated schematically in FIG. 4. The dialysis solution circulatory system comprises two continuous flow heaters $H_1$ and $H_2$ as well as three temperature measuring sensors which measures the temperature $T_1$, $T_2$, and $T_3$. The temperature sensor $T_2$ and the continuous flow heater $H_3$ form together with the electronic regulator 27 of the conventional construction, a temperature control system 28 within a control device which serves to bring the temperature of the dialysis solution supplied to the dialyzer to an adjustable, rated value which corresponds about to the human body temperature (about 38° C.). One must assume that the temperature of the used-up dialysis solution coming from the dialyzer is lower than the temperature of the solution supplied to the dialyer because of heat losses to the enviroment. Thus, the temperature sensor which measures the temperature $T_3$ senses a lower temperature at the connection of the connection of the return flow conduit 3a connected to the balancing device. In order to provide the same conditions for both components 1a and 1b of the balancing device, the temperature measured by the temperature sensor $T_3$ is used as a rated value for a temperature regulating system which comprises the temperature sensor $T_1$, the continuous flow heater $H_1$ and an electronic controller. This regulating system causes the equalization of the temperatures $T_1$ and $T_3$.

The invention provides in another embodiment that the temperature dependency of the density and the influence caused thereby on the balancing is taken into account by calculation. In connection with an exact volumetric balancing the balancing error caused by a temperature deviation and which is dependent on the masses given by the formula:

$$\Delta m = 0.167 Q_D \cdot (T_3 - T_1) \beta$$

wherein $\Delta m$ is given in grams per hour. $Q_D$ is the dialysis solution flow in grams per minute, $T_3 - T_1$ is a temperature difference in degrees Kelvin between the inlets of the balancing device and $\beta$ is the cubic expansion coefficient of the dialysis solution, about $3.7 \times 10^{-4}$ °$K^{-1}$. A signal proportional to the resulting calculation may be used to control the withdrawing device 7 and the rate of ultra-filtration.

The technical performance of the calculation operation is possible in different ways. The block circuit diagram of FIG. 5 which represents a preferred embodiment, is based on the assumption that the entire quantity of the ultra-filtrate is displayed on a display device 30, for example, a digital display device. The display device is controlled by a counter or computer circuit 31, the input pulses of which represent a respective, determined unit quantity of the ultra-filtrate (for example, one gram). The counter receives input pulses through an OR-gate 32 from the withdrawal device 7 in FIG. 1 as well as from the correction circuit for compensating the temperature influence. If the withdrawal device is a volumetric pump which conveys a unit volume per work stroke, the control pulses of the pump may be applied directly to the input 33 of the OR-gate. In other instances it may be necessary to use, for example, an intermediate circuit comprising a voltage frequency converter.

For correcting the influence of the temperature difference $T_1-T_3$ first the difference between the two electric signals is formed which represent the temperatures $T_1$ and $T_3$, said difference being formed by means of the subtraction circuit 34. The difference $T_1-T_3$ is multiplied by the multiplier 35 by an electrical signal corresponding to the through flow $Q_D$. If the machine operates always with the same dialysis solution flow and if no operation adjustment for this flow is provided, it is possible to avoid the multiplier altogether and to take the through flow rate into account as a constant factor just as the other constants.

Thereafter the signal is supplied to a voltage frequency converter 36 which produces a pulse frequency corresponding to the temperature difference and to the other influencing magnitudes, said pulse frequency representing unit quantities per unit of time. These pulses are supplied to the input 37 of the OR-gate 32. If the two input signals of the OR-gate have a pulse duration which is very small relative to the pauses between the impulses, the respective error which could occur due to a random coincidence between two pulses, may be disregarded. Where a computer circuit is used, for example at 31 of FIG. 5 the calculation of the volumetric balancing correction factor may be completed to provide a signal output for control of the ultra-filtrate withdrawing pump 7. In this respect, the rate of ultra-filtration across the dialyzer membrane may be automatically controlled.

Figure 5:
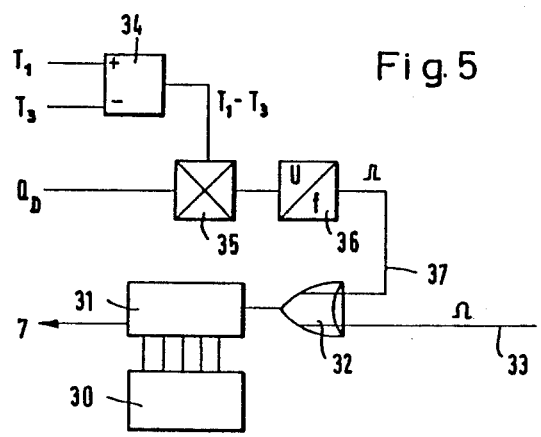
FIG. 5 is a block circuit diagram for calculating the compensation of the influence of temperature differences.

The arrangement shown in FIG. 5 represents but one example of a possible embodiment. When the apparatus comprises a micro-computer, for example, for other purposes, it is suggested to use the microcomputer for the present purpose. Starting from the basic arrangement shown in FIG. 2, different embodiments of the dialysis solution circulatory system are possible, whereby the difference may relate to the production of the throughflow in the dialyzer as well as to the removal of air from the dialyzer circulatory system. Where circuit 31, for example, is a micro-computer, various control functions such as those mentioned above, may be included.

Figure 4:
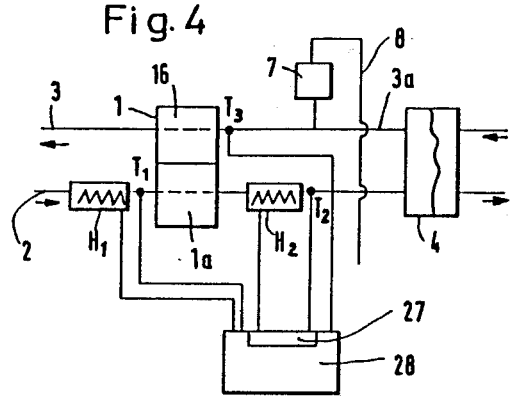
FIG. 4 is a further embodiment of the arrangement according to FIG. 1 for compensating temperature caused errors in the mass balance.
Figure 6:
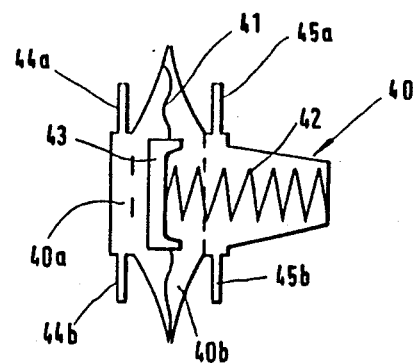
FIG. 6 shows a schematic sectional view of an example of a balancing chamber.

In an embodiment of the balancing chambers of the type shown schematically in FIG. 4 having a passively displaceable separation element in the chamber, namely, the membranes 24 and 25, it is necessary to provide an additional conveying device in series with the dialyzer in order to produce the through flow. A pump of any type is suitable for this purpose. However, there is also the possibility to construct the balancing chambers according to the principle illustrated in FIG. 6.

The balancing chamber 40 is separated into two chambers 40a and 40b by means of one movable or rather displaceable membrane 41. An energy storing device in the form of a coil spring 42 is arranged in one of the two chambers. The spring 42 rests against a support element 43 solidly connected to the membrane 41 in a sealing manner. In the position shown in FIG. 6, the to spaces in balancing chamber 40 are in equilibrium. The spring 42 is so dimensioned that it may displace the support element 43 all the way to the outer wall of the space 40a and to retain a residual force in this position.

In this manner the spring provides the driving force for the transport of the liquid out of the space 40a. The through flow speed depends on the through flow resistance of the closed liquid circulatory system and may be adjusted by means of a throttle to the desired value. The space 40a comprises for its filling and emptying connecting ports 44a and 44b, whereas the space 40b is provided with connecting ports 45a and 45b.

The just described function of the balancing system assumes in any event that the medium present in the balancing chambers is practically incompressible. Thus, it must be prevented that air bubbles enter into the balancing chambers. On the input side for the supply of fresh dialysis solution this condition is assured without any difficulties because it is necessary anyway to degas the dialysis solution before it reaches the dialyzer. For this purpose devices are known operating with a thermal or reduced pressure degassing and a subsequent removal of the gas bubbles.

According to the invention, a further air separator is necessary on the return flow side from the dialyzer to the balancing device in order to remove air which may enter the system, particularly due to leaks at the dialyzer connections or in other uncontrollable ways.

Figure 7:
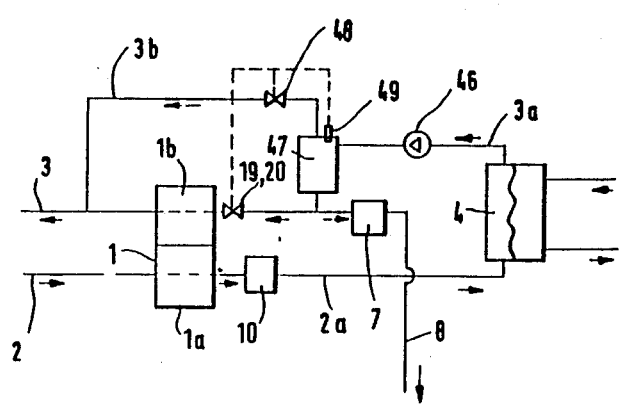
FIG. 7 is another extended embodiment of the arrangement according to FIG. 1 for venting the dialyzer circulatory system.

FIG. 7 shows a respective arrangement which comprises in addition to the functional elements described with reference to FIGS. 1 and 2, a pump 46, an air separator container 47, and an air separator valve 48. The air separator valve 48 is controlled by a level sensor 49. If the liquid level in the air separator container 47 sinks to such an extent that the level sensor responds, due to the air collected in the air separator container 47, the air separator valve 48 is opened in the conduit 3b which connects to the discharge conduit 3. In order to produce a positive pressure in the air discharge container 47 by utilizing the drive force 'd' of the pump 46, the return flow in the balancing device is additionally closed off in a suitable manner when the level sensor 48 responds.

For example, this may be accomplished by closing the valves 19 and 20 (FIG. 3) as schematically indicated in FIG. 7. The collected air is discharged through the air discharge valve 48. The level sensor 49 may for instance, be a reed contact which is actuated by a magnet provided with a float. The switching characteristic of the reed contact may be utilized advantageously for terminating the air removal when the liquid level in the removal chamber again exceeds a predetermined liquid level.

An example embodiment of a hemodialysis apparatus that has been constructed and which combines certain of the above described features as well as a few additional features will now be described with reference to FIG. 8, whereby the same components as in FIGS. 1 to 4 and 7 are provided with the same reference numbers.

Figure 8:
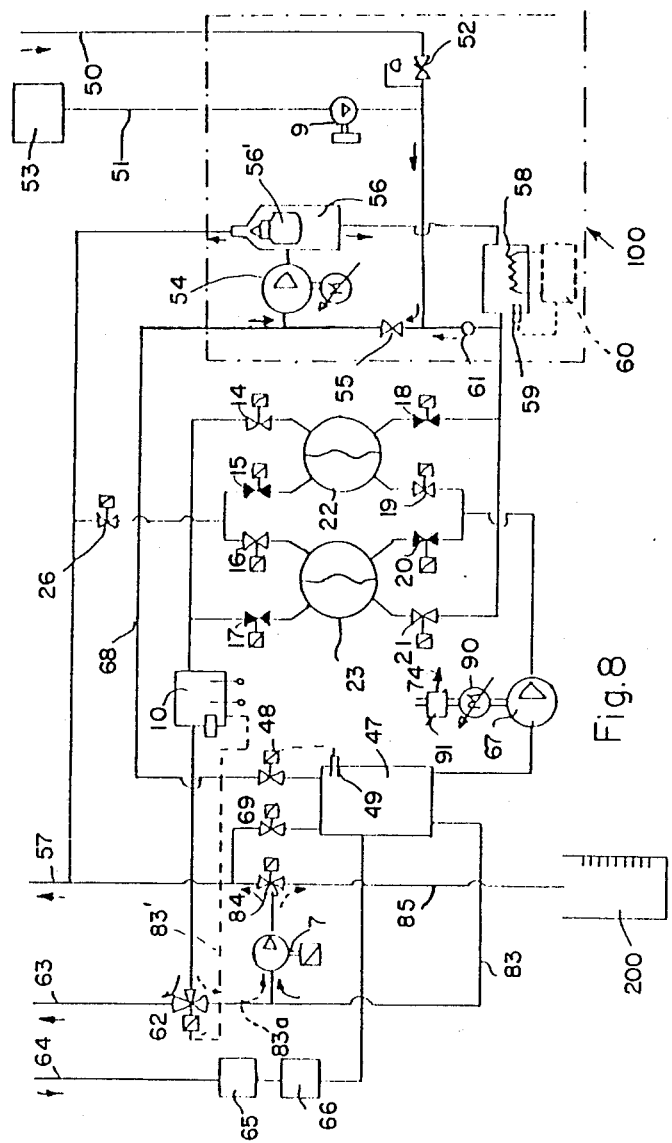
FIG. 8 is a detailed illustration of the liquid circulatory system of a hemodialyzing apparatus.
Figure 8A:
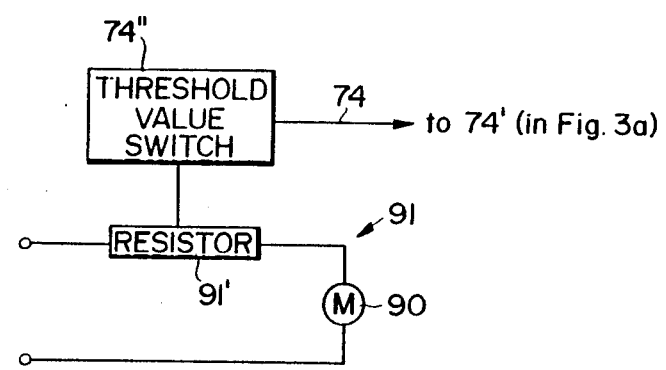
FIG. 8A shows a detail of the circuit of a pump motor of FIG. 8.

The liquid circulatory system schematically shown in FIG. 8 comprises as an essential component the balancing device already shown in FIG. 3 including the two balancing chambers 22 and 23 and the respective valves 14 to 21.

The supply of fresh dialysis solution to the balancing device takes place under a certain pressure (about 0.3 to 1.5 tar) from the supply unit 100 which, among others, also serves for degassing and heating the dialysis solution. The water entering through the water conduit 50 is reduced in its pressure by the pressure reduction valve 52 to a lower pressure (0.1 to 1.0 bar).

The concentrate is admixed downstream of the pressure reduction valve. The concentrate is taken out of a concentrate container 53 through the dosing apparatus 9 and the conduit 51.

Figure 9:
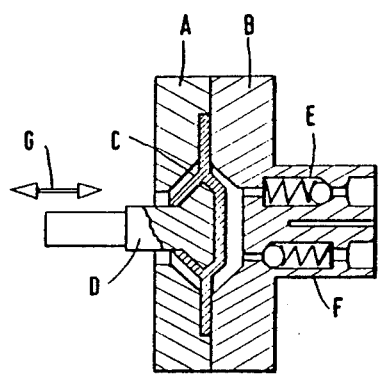
FIG. 9 is a sectional view through an example embodiment of a dosing apparatus.

The dosing apparatus shown in FIG. 9 purely schematically has a housing A, B in which the membrane body C (for example, rubber) is located. A plug end D is vulcanized into the membrane body and driven with a defined, if desired adjustable, stroke in the direction of the double arrow G.

The non-return valves E, F are located on the other side of the membrane housing.

As explained with reference to FIG. 3 the operation of the dosing apparatus 9 is synchronized with the control of the balancing device so that for each work stroke of the balancing device a corresponding work stroke or a defined number of work strokes of the dosing apparatus are caused. The mixture is degassed by the reduced pressure (about −0.9 bar) produced by the pump 54 in combination with the flow resistance 55. The flow resistance may either be constructed as a simple throttle or it may be a control valve controlled by the reduced pressure.

The liberated air is separated through the air separator 56 and, for example, conducted into the discharge conduit 57. Ihe air separator 56 may, as indicated, work with a float 56′ controlled air outlet, or with a level sensor which actuates a magnetic valve.

The degassed dialysis solution travels from the lower connection of the air separator 56 through the continuous flow heater 58 to the balancing device. The continuous flow heater comprises an electrical heater and at least one temperature sensor 59. The continuous flow heater heats the dialysis solution to a temperature corresponding to about body temperature (38° C.). For this purpose the temperature sensor 59 and the heater 58 are operatively interconnected through a temperature control 60 in a known manner.

The balancing device, as explained with reference to FIG. 3, is charged in sequential work strokes with fresh dialysis solution of determined quantities which are defined by the volume of the balancing chambers 22 and 23. The dialysis solution travels during the pauses between the charging work strokes through the overflow valve 61 again into the degassing system. The dialysis solution flows during this time in a closed loop circulatory system formed by the elements 54, 56, 58, 61, and 55. The mentioned high reduced pressure is always available at the suction side of the pump 54. This high reduced pressure is used in the example described here also for the purpose of removing the air from the air separator 47 located in the dialyzer circulatory system.

Referring to FIG. 8, the arrangement of the elements 54, 55, 56, 58, 61 in a closed loop re-circulatory system is a special feature of the supply unit 100 and so is the feeding of the dialysis solution into the connecting conduit forming a junction between the flow resistance 55 and the pressure maintaining valve 61. A high efficiency in the degassing and an advantageous control characteristic of the continuous flow heater are achieved due to the re-circulation. Another advantage is seen in that in this embodiment the dialysis solution is available under pressure which may be higher to any desirable extent than the water inlet pressure at 50. another advantage is seen in that simultaneously a reduced pressure is available for sucking off of air out of other components of the system. Although the closed loop arrangement of the elements 55, 54, 56, 61 is essential, the continuous flow heater 58 could be arranged at another position of the circulatory system, for example, directly ahead of the flow resistance 55 or between the flow resistance and the pump 54 or between the pump and the air separator 56.

The fresh dialysis solution coming from the balancing device travels through the analyzing device 10 and the bypass valve 62 in the conduit 63 leading to the dialyzer. The valve 62 is connected electrically by a dashed line 83′ to the analyzer 10 for controlling the operation of the valve 62. The analyzing device 10 is, in the present instance, an electrical conductivity meter combined with a temperature sensor which serves on the one hand for the compensation of the temperature dependency of the conductivity measurement and which, on the other hand, is used for measuring and monitoring the temperature of the dialysis solution as explained above with reference to FIG. 4. If the conductivity or the temperature is outside the permissible standard range, the bypass valve 62 is automatically switched over so that the dialysis solution is not supplied anymore to the dialyzer, but rather it is detoured in accordance with the dashed arrow to the discharge side of the dialyzer.

During the normal function of the dialysis, solution coming from the dialyzer flows through the conduit 64, through the blood leakage detector 65, and through the pressure measuring device 66 into the air separator 47. The blood leakage detector and the pressure measuring device are known components for monitoring the leak tightness of the dialyzer membrane or for measuring the return flow pressure. The used-up dialysis solution is returned from the lower portion of the air separator 47 through the pump 67 to the balancing device. The conveying capacity of this pump, which may, for example, be varied by an r.p.m. adjustment of the drive motor 90 determines the quantity of dialysis solution flowing per time unit through the dialyzer.

The electrical signal 74 for the switch over of the valves of the balancing device and for the synchronous control of the dosing apparatus 9 is derived, in the actual embodiment of a hemodialysis apparatus, from the supply circuit 91 of the drive motor 90 of the pump 67. If, namely, the membrane which forms a displaceable element in the respective balancing chamber serving for the supply of the dialyzer, reaches an end position when it rests completely against the chamber wall, the power requirement and thus the current taken up by the pump motor 90 rise sharply. In this manner it is possible to derive the switch over signal by means of a resistor 91′ inserted into the motor current circuit including the supply circuit 91 for the motor 90, said resistor 91′ being connected with the input of a threshold value switch 74″. The switch over signal 74 from the threshold value switch 74" is applied to the input 74' of FIG. 3A when said motor current rises sharply.

The air separator chamber 47 has in its upper portion a level sensor 49, for example, including a preheated thermistor operating in accordance with another conventional functional principle. If the liquid level in the air separating chamber 47 falls below the response level of the sensor 49, the valve 48 is opened by the switching signal of the sensor 49 so that the air is sucked off through the conduit 68 through the degassing pump 54 into the supply section 100. A reduced pressure of, for example, −0.9 bar is used for removing the air because in the dialyzer circulatory system also normally a reduced pressure prevails ranging up to about −0.6 bar depending on the adjusted ultra-filtration rate.

The valve 48 is closed again when the liquid level in the air separating chamber 47 has risen again sufficiently.

For the connection of a dialyzer which is not prefilled with the liquid, a special filling program is provided as has been explained above with reference to FIGS. 3 and 3A. The balancing function is suspended in the filling program. However, the proportional dosing function of the balancing device in combination with the dosing apparatus 9 is maintained.

The filling program is switched on automatically when the air removal operation through the valves 48 exceeds a predetermined duration due to the large quantity of air coming from the dialyzer. For example, the filling program may be switched on by closing the switches 75a and 75b in FIG. 3A through a timer which is connected with the sensor 49.

In this instance the valve 48 is closed and a valve 69 is opened in order to conduct the air through this valve directly to the discharge port 57. The valve control is modified in the manner described with reference to FIGS. 3 and 3A so that fresh dialysis solution is supplied unbalanced to the dialyzer where it displaces the air present in the dialyzer into the air separator container 47. Thus, the air flows through the opened valve 69 into the discharge port or conduit 57. If the liquid level in the air separator container has risen again due to the following dialysis solution, the filling program is terminated by the respective signal of the level sensor 49 and the system is switched over again to the normal balancing type of operation.

The removal of a precisely predetermined liquid quantity from the dialyzer circulatory system and thus the measuring and/or control of the ultra-filtration takes place by means of the withdrawal device 7. The withdrawal device 7 is constructed, in the present example embodiment as a volumetric membrane pump, whereby each individual pump stroke corresponds to a quantity unit (1 milliliter) of ultra-filtrate. The withdrawal takes place through a conduit 83 from the lower portion of the air separator container 47 in order to make sure that only liquid free of bubbles is being conveyed. The output of the ultra-filtration pump or withdrawal device 7 is normally connected with the discharge port or conduit 57 through the switch over valve 84. However, with the aid of the switch over valve 84 there is also the possibility to separately discharge the withdrawn liquid in accordance with the dashed arrow through the sample conduit 85, and, for example, to gather the withdrawn liquid in a measuring container 200 for control purposes. Thus, the rate of ultra-filtration may be regulated by a measurement signal for controlling the pump 7 as heretofore described.

For example, a signal representing the measured quantity of withdrawn or diverted ultra-filtrate solution may be used to control the rate of the volumetric pump 7 to maintain a specified rate of withdawal or to achieve a desired quantity of withdrawn ultra-filtrate containing solution. As one example, the pump may be regulated for withdrawing a fractional portion in the order of magnitude of 1/1000 of the total ultra-filtrate containing solution flow downstream from the dialyzer in the dialysis solution circulatory system. Additionally, the withdrawing or diverting pump 7 may be regulated to maintain volumetric balance and equivalence between the upstream dialysis solution flowing into the dialyzer and the downstream ultra-filtrate containing solution flowing away from or leaving the dialyzer despite temperature changes and differences, all as heretofore described.

Another characteristic feature resides in that the samples of the fresh dialysis solution may also be taken through the connection of the inlet to the bypass conduit 83 and through a suitable utilization of the switch over valves 62 and 84, whereby the samples are taken through the sample conduit 85, for example, in order to control the composition of the dialysis solution by means of an external analyzing apparatus. For this purpose the valves 52 and 84 are brought into the positions represented by the dashed arrows, by means of a selector switch, not shown, and the ultra-filtration pump is switched to its maximal stroke frequency. The dialysis solution is then available in the sample conduit 85.

Incidentally, a significant difference relative to prior art proportional dosing arrangements in hemodialysis devices resides in that in the apparatus according to the invention the concentrate and the dialysis solution are dosed whereas in prior art devices the original components, namely, water and concentrate are dosed. Due to this feature the apparatus according to the invention provides an essential advantage with regard to the chemical disinfection of the apparatus. It is conventional and suitable to supply a concentrate of a disinfectant instead of the concentrate used for the production of the dialysis solution, when the dialysis solution circulatory system is subjected to a chemical disinfection between treatments. Such disinfectant concentrate provides the disinfection solution after dilution with water. In prior art proportional dosing devices this means that all components located between the water faucet of the apparatus and the dosing apparatus for the water as well as the dosing apparatus itself are not included in the chemical disinfection because the addition of the concentrate takes place downstream of the dosing apparatus. Contrary thereto in the system used according to the invention the concentrate dosing apparatus may, for example, be connected directly to the water inlet of the apparatus so that the entire liquid conducting portion of the apparatus is included in the disinfection.

Incidentally, the main advantages of the supply unit 100 shown in FIG. 8 is seen in that the degassing device or air separator 56 is located at a point in the entire conduit system where the largest reduced or negative pressure prevails. Thus, gas that may be present in solution in the conduit system is subject to a suction effect causing the gas to be drawn into the separator 56. Yet another important advantage of this arrangement is seen in that the production of fresh dialysis solution is easiest in this zone of reduced or negative pressure.

Although the invention has been described with reference to specific example embodiments, it will be appreciated that it is intended to cover all modifications and equivalents within the scope of the appended claims.

What is claimed is:

1. A hemodialysis apparatus, comprising dialyzer means (4, 5), fresh dialysis solution supply means (50, 51, 52, 53, 54) and used dialysis solution discharge means (57, 85), said dialyzer means (4, 5) including a dialyzer housing (4) and a semi-permeable membrane (5) dividing said dialyzer housing into a dialyzing chamber means and into blood chamber means connectable to a patient, said dialyzing chamber means having an inlet and an outlet, first conduit means connected at one end thereof to said blood chamber means and connectable at another end thereof to a patient, second conduit means connected to said inlet and outlet of dialyzing chamber means, to said fresh dialysis solution supply means, and to said used dialysis solution discharge means for providing a flow circuit therebetween, said fresh dialysis solution supply means comprising two balancing chambers (22, 23), a movable element (24, 25) in each of said two balancing chambers (22, 23) for dividing each of said balancing chambers into two balancing spaces (22a, 22b and 23a, 23b) thereby providing a total of four balancing spaces, a first set of controllable valve means (14, 17, 18, 21) in said second conduit means for alternately connecting one balancing space (22a or 23a) of a first group of two (22a, 23a) of said four balancing spaces to said inlet of said dialying chamber means and to said fresh dialysis solution supply means to alternately supply fresh dialysis solution into said dialyzing chamber means from said fresh dialysis solution supply means through said first group of two balancing spaces, a second set of controllable valve means (15, 16, 19, 20) in said second conduit means for alternately connecting one balancing space (22b or 23b) of a second group of two (22b, 23b) of said four balancing spaces to said outlet of said dialyzing chamber means and to said used dialysis solution discharge means to alternately discharge used dialysis solution from said dialyzing chamber means into said used dialysis solution discharge means through said second group of two balancing spaces, said second conduit means forming a closed dialysis solution circulating circuit between said dialyzing chamber means and the respective one of said balancing chambers, means connected to said closed dialysis solution circuliating circuit for removing a determined quantity of ultrafiltrate from said closed dialysis solution circulating circuit, first degassing means (56) connected to said fresh dialysis solution supply means and to said first group of two balancing spaces for supplying degassed fresh dialysis solution into said first group of two balancing spaces, second degassing means connected to said outlet of said dialyzing chamber means and to said second group of two balancing spaces for supplying degassed used dialysis solution into said second group of two balancing spaces, whereby always fresh degassed dialysis solution is balanced against used degassed dialysis solution, pump means operatively connected to said second conduit means for crculating dialysis solution in said closed dialysis solution circulating circuit, and control means operatively connected to said first and second sets of controllable valve means for operating said first and second sets of controllable valve means so that one balancing space of said first group of balancing spaces reoeives fesh dialysis solution while the other balancing space of said first group of balancing spaces supplies fresh dialysis solution into said dialyzing chamber means, and so that one balancing space of said second group of balancing spaces discharges used dialysis solution while the other balancing space receives used dialysis solution, whereby one balancing chamber is being filled with fresh dialysis solution, thereby discharging used dialysis solution while the other balancing chamber is being filled with used dialysis solution from said dialyzing chamber means, thereby discharging fresh dialysis solution into said dialyzing chamber means and vice versa, wherein said pump means include a variable capacity pump and a pump motor for driving said variable capacity pump, and wherein said control means for said first and second sets of controllable valve means operate said first and second sets of controllable valve means so that the charging of fresh dialysis solution into one balancing chamber presently disconnected from said inlet of said dialyzing chamber means, is already completed when a supply of fresh dialysis solution from the other balancing chamber into the dializing chamber means becomes exhausted.

2. The apparatus of claim 1, wherein said control means for said first and second sets of controllable valve means comprise sensor means operatively arranged for sensing end positions of said movable elements to thereby switch-over said sets of controllable valve means in response to said movable elements reaching a respective end position, whereby a switch-over signal is derived from that balancing chamber which is presently connected to said closed dialysis solution circulating circuit.

3. The apparatus of claim 2, wherein said fresh dialysis soluion supply means comprise mixing means connected to a source of water and to a source of dialysis concentrate, and dosing means connected to said mixing means for supplying said dialysis concentrate to said mixing means, said control means being also connected to said dosing means for controlling the dosing means also in response to said movable elements reaching an end position, whereby a dosing operation is cased for each switch over of said first and second sets of controllable valve means.

4. The apparatus of claim 1, further comprising means for monitoring a concentration of said fresh dialysis solution flowing to said inlet of said dialyzing chamber means.

5. The apparatus of claim 1, further comprising third conduit means (68) operatively interconnecting said first and second degassing means, further valve means (48) in said third conduit means, operating means connected to said further valve means, fluid level sensor means (49) in said second degassing means (47) for said used dialysis solution, connected to said operating means of said further valve means (48) for operating said further valve means (48) in response to a fluid level in said second degassing means (47).

6. The apparatus of claim 1, comprising further valve means (48) operatively connected to said second degassing means for venting said second degassing means (47).

7. The apparatus of claim 6, further comprisign a level sensor (49) in said second degassing means (47) for sensing a liquid level in said second degassing means and for operating said further valve means in response to a certain liquid level in said second dagassing means.

8. The apparatus of claim 1, further comprising a bypass conduit (83) connected to said second degassing means, volumetric pump means (7) having an inlet connected to said bypass conduit and a pump outlet, ultrafiltrate sample conduit means (85) connected to said pump outlet for gathering liquid withdrawn from said second degassing means into a measuring container.

9. A hemodialysis apparatus, comprising dialyzer means (4, 5), fresh dialysis solution supply means (50, 51, 52, 53, 54) and used dialysis solution discharge means (57, 85), said dialyzer means (4, 5) including a dialyzer housing (4) and a semi-permeable membrane (5) dividing said dialyzer housing into a dialyzing chamber means and into blood chamber means connectable to a patient, said dialyzing chamber means having an inlet and an outlet, first conduit means connected at one end thereof to said blood chamber means and connectable at another end thereof to a patient, second conduit means connected to said inlet and outlet of said dialyzing chamber means, to said fresh dialysis solution supply means, and to said used dialysis solution discharge means for providing a flow circuit therebetween, said fresh dialysis solution supply means comprising two balancing chambers (22, 23), a movable element (24, 25) in each of said two balancing chambers (22, 23) for dividing each of said balancing chambers into two balancing spaces (22a, 22b and 23a, 23b) thereby providing a total of four balancing spaces, a first set of controllable valve means (14, 17, 18, 21) in said second conduit means for alternately connecting one balancing space (22a or 23a) of a first group of two (22a, 23a) of said four balancing spaces to said inlet of said dialyzing chamber means and to said fresh dialysis solution supply means to alternately supply fresh dialysis solution into said dialyzing chamber means from said fresh dialysis solution supply means through said first group of two balancing spaces, a second set of controllable valve means (15, 16, 19, 20) in said second conduit means for alternately connecting one balancing space (22b or 23b) of a second group of two (22b, 23b) of said four balancing spaces to said outlet of said dialyzing chamber means and to said used dialysis solution discharge means to alternately discharge used dialysis solution from said dialyzing chamber means into said used dialysis solution discharge means through said second group of two balancing spaces, said second conduit means forming a closed dialysis solution circulating circuit between said dialyzing chamber means and the respective one of said balancing chambers, ultrafiltrate pump means (7) connected to said closed dialysis solution circuilating circuit for removing a determined quantity of ultrafiltrate from said closed dialysis solution circulating circuit, first degassing means (56) connected to said fresh dialysis solution supply means and to said first group of two balancing spaces for supplying degassed fresh dialysis solution into said first group of two balancing spaces, second degassing means (47) connected to said outlet of said dialyzing chamber means and to said second group of two balancing spaces for supplying degassed used dialysis solution into said second group of two balancing spaces, whereby always fresh degassed dialysis solution is balanced against used degassed dialysis solution, circulation pump means (67) operatively connected to said second conduit means for circulating dialysis solution in said closed dialysis solution circulating circuit, and control means operatively connected to said first and second sets of controllabel valve means for operating said first and second sets of controllable valve means so that one balancing space of said first group of balancing spaces receives fresh dialysis solution while the other balancing space of said first group of balancing spaces supplies fresh dialysis solution into said dialyzing chamber means, and so that one balancing space of said second group of balancing spaces discharges used dialysis solution while the other balancing space receives used dialysis solution, whereby one balancing chamber is being filled with fresh dialysis solution, thereby discharging used dialysis solution while the other balancing chamber is being filled with used dialysis solution from said dialyzing chamber means, thereby discharging fresh dialysis solution into said dialyzing chamber and vice versa, said ultrafiltrate pump means for removing a determined quantity of ultrafiltrate from said closed dialysis solution circulating circuit comprising a volumetric pump (7) delivering a precisely predetermined liquid quantity with each individual pump stroke, said ultrafiltrate pump means (7) being connected with its suction inlet to a bubble-free part of said closed dialysis solution circulating circuit, said circulation pump means (67) having a suction inlet also connected to an outlet of said second degassing means (47) for maintaining used dialysis liquid at a reduced pressure at all times to keep gasses from entering into solution in said used dialysis liquid.

10. The apparatus of claim 9, wherein said volumetric pump is a membrane pump.

11. The apparatus of claim 9, wherein said second degassing means (47) comprise an air separator chamber (47) having a dialysis liquid inlet means and dialysis liquid outlet means and an air outlet in an upper portion of said air separator chamber, means for controlling the level of dialysis liquid in said air separator chamber (47), and a degassing pump means (54) connected by a conduit (68) with said air outlet, said degassing pump means (54) providing in said air separator chamber (47) a reduced pressure which is more intensive than a reduced pressure caused by said means for removing a determined quantity of ultrafiltrate.

12. The apparatus of claim 11, wherein said means for controlling the level of dialysis liquid in said air separator chamber (47) comprise a liquid level sensor (49) and a valve (48) connected in said conduit (68) between said air outlet and said degassing pump means (54), said valve (48) being operable in response to a switching signal from said level sensor (49).

13. A homodialysis apparatus, comprising dialyzer means (4, 5), fresh dialysis solution supply means (50, 51, 52, 53, 54) and used dialysis solution discharge means (57, 85), said dialyzer means (4, 5) including a dialyzer housing (4) and a semi-permeable membrane (5) dividing said dialyzer housing into a dialyzing chamber means and into blood chamber means connectable to a patient, said dialyzing chamber means having an inlet and an outlet, first conduit means connected at one end thereof to said blood chamber means and connectable at another end thereof to a patient, second conduit means connected to said dialyzing chamber means, to said fresh dialysis solution supply means, and to said used dialysis solution discharge means for providing a flow circuit therebetween, said fresh dialysis solution supply means comprising two balancing chambers (22, 23), a movable element (24, 25) in each of said two balancing chambers (22, 23) for dividing each of said balancing chambers into two balancing spaces (22a, 22b and 23a, 23b) thereby providing a total of four balancing spaces, a first set of controllable valve means (14, 17, 18, 21) in said second conduit means for alternately connecting one balancing space (22a or 23a) of a first group of two (22a, 23a) of said four balancing spaces to said inlet of said dialyzing chamber means and to said fresh dialysis solution supply means to alternately supply fresh dialysis solution into said dialyzing chamber means from said fresh dialysis solution supply means through said first group of two balancing spaces, a second set of controlable valve means (15, 16, 19, 20) in said second conduit means for alternately connecting one balancing space (22b or 23b) of a second group of two (22b, 23b) of said four balancing spaces to said outlet of said dialyzing chamber means and to said used dialysis solution discharge means to alternately discharge used dialysis solution from said dialyzing chamber means into said used dialysis solution discharge means through said second group of two balancing spaces, said second conduit means forming a closed dialysis solution circulating circuit between said dialyzing chamber means and the respective one of said balancing chambers, means connected to said closed dialysis solution circulating circuit for removing a determined quantity of ultrafiltrate from said closed dialysis solution circulating circuit, first degassing means (56) connected to said fresh dialysis solution supply means and to said first group of two balancing spaces for supplying degassed fresh dialysis solution into said first group of two balancing spaces, second degassing means (47) connected to said outlet of said dialyzing chamber means and to said second group of two balancing spaces for supplying degassed used dialysis solution into said second group of two balancing spaces, whereby always fresh degassed dialysis solution is balanced against used degassed dialysis solution, pump means operatively connected to said second conduit means for circulating dialysis solution in said closed dialysis solution circulating circuit, and control means operatively connected to said first and second sets of controllable valve means for operating said first and second sets of controllable valve means so that one balancing space of said first group of balancing spaces receives fresh dialysis solution while the other balancing space of said first group of balancing spaces supplies fresh dialysis solution into said dialyzing chamber means, and so that one balancing space of said second group of balancing spaces discharges used dialysis solution while the other balancing space receives used dialysis solution, whereby one balancing chamber is being filled with fresh dialysis solution, thereby discharging used dialysis solution while the other balancing chamber is being filled with used dialysis solution from said dialyzing chamber means, thereby discharging fresh dialysis solution into said dialyzing chamber and vice versa, said second degassing means (47) comprising an air separator chamber (47) having dialysis liquid inlet means and dialysis liquid outlet means and an air outlet in an upper portion of said air separator chamber, means for controlling the level of dialysis liquid in said air separator chamber (47), and a degassing pump means (54) connected by a conduit (68) with said air outlet, said degassing pump means (54) providing in said air separator chamber (47) a reduced pressure which is more intensive than a reduced pressure caused by said means for removing a determined quantity of ultrafiltrate.

* * * * *

UNITED STATES PATENT AND TRADEMARK OFFICE
CERTIFICATE OF CORRECTION

PATENT NO. : 4,770,769

DATED : September 13, 1988

INVENTOR(S) : Wilfried Schael

It is certified that error appears in the above-identified patent and that said Letters Patent is hereby corrected as shown below:

Column 19, line 47, replace "circuilating" by
--circulating--;
          line 60, replace "crculating" by
--circulating--;
          line 66, replace "reoceives" by --receives--;
          replace "fesh" by --fresh--;
Column 20, line 32, replace "soluion" by --solution--;
          line 39, replace "cased" by --caused--;
          line 60, replace "comprisign" by --comprising--;
          line 64, replace "dagassing"" by --degassing--;
Column 21, line 46, replace "circuilating" by --circulating--;
          line 63, replace "controllabel" by --controllable--;
Column 22, line 11, replace "ultrafiltate" by --ultrafiltrate--;
          line 58, replace "sald" by --said--.

Signed and Sealed this

Third Day of January, 1989

Attest:

DONALD J. QUIGG

Attesting Officer      Commissioner of Patents and Trademarks